(12) United States Patent
Rossel

(10) Patent No.: US 12,115,175 B2
(45) Date of Patent: Oct. 15, 2024

(54) ORAL DOSAGE FORM FOR ENHANCED SOLUBILIZATION OF A POORLY SOLUBLE ACTIVE AGENT AND METHOD OF PREPARATION

(71) Applicant: OYSTERSHELL NV, Merelbeke (BE)

(72) Inventor: Bart Rossel, Merelbeke (BE)

(73) Assignee: OYSTERSHELL NV, Merelbeke (BE)

( * ) Notice: Subject to any disclaimer, the term of this patent is extended or adjusted under 35 U.S.C. 154(b) by 131 days.

(21) Appl. No.: 16/476,019

(22) PCT Filed: Jan. 8, 2018

(86) PCT No.: PCT/EP2018/050383
§ 371 (c)(1),
(2) Date: Jul. 3, 2019

(87) PCT Pub. No.: WO2018/127594
PCT Pub. Date: Jul. 12, 2018

(65) Prior Publication Data
US 2019/0343849 A1    Nov. 14, 2019

(30) Foreign Application Priority Data

Jan. 6, 2017  (EP) .................................. 17150552
Feb. 21, 2017  (BE) ................................ 2017/5106

(51) Int. Cl.
*A61K 31/661*  (2006.01)
*A61K 9/16*  (2006.01)
(Continued)

(52) U.S. Cl.
CPC .......... *A61K 31/661* (2013.01); *A61K 9/1635* (2013.01); *A61K 9/1652* (2013.01);
(Continued)

(58) Field of Classification Search
CPC ..................................................... A61K 31/661
See application file for complete search history.

(56) References Cited

U.S. PATENT DOCUMENTS

2004/0170681 A1* 9/2004 Grattan ................ A61K 9/2009
424/465
2004/0180088 A1  9/2004 Dudhara et al.
(Continued)

FOREIGN PATENT DOCUMENTS

DE   198 59 231 A1   6/2000
WO   01/15665 A1   3/2001
(Continued)

OTHER PUBLICATIONS

Singh, B.N et al. "Floating drug delivery systems: an approach to oral control led drug delivery via gastric retention." Journal of Controlled Rele, Elsevier, Amsterdam, NL, vol. 63, No. 3, Feb. 3, 2000, pp. 235-259, XP004244475.
(Continued)

*Primary Examiner* — Sarah Alawadi
(74) *Attorney, Agent, or Firm* — Vorys, Sater, Seymour and Pease LLP

(57) ABSTRACT

The present invention provides and oral dosage form comprising a granular phase and a non-granular phase, whereby the granular phase is comprised of a therapeutically effective amount of pharmaceutically active agent, a gas forming agent and a hydrophilic polymer. Such dosages are found to provide fast dissolution rates for ingredients having low solubility in water. In addition, the present invention provides a method of preparation thereof.

12 Claims, 2 Drawing Sheets

(51) Int. Cl.
  *A61K 31/19*    (2006.01)
  *A61K 31/4415*  (2006.01)
  *A61K 33/08*    (2006.01)
(52) U.S. Cl.
  CPC .......... *A61K 31/19* (2013.01); *A61K 31/4415* (2013.01); *A61K 33/08* (2013.01)

(56) References Cited

U.S. PATENT DOCUMENTS

2005/0220865 A1    10/2005  Koleng et al.
2010/0305071 A1*   12/2010  Kligerman ............. A61K 31/66
                                                  514/129
2015/0272937 A1*   10/2015  Fathi .................... A61K 33/08
                                                  424/472
2015/0374725 A1*   12/2015  Kligerman ............. A61K 45/06
                                                  424/489

FOREIGN PATENT DOCUMENTS

WO    2004/032906 A1    4/2004
WO    2005/097078 A1    10/2005
WO    2009/150323 A1    12/2009

OTHER PUBLICATIONS

PCT International Search Report for PCT Application No. PCT/EP2018/050383, dated Mar. 14, 2018, in 3 pages.
International Preliminary Report on Patentability for PCT Application No. PCT/EP2018/050383, dated Jan. 10, 2019 in 14 pages.

* cited by examiner

ORAL DOSAGE FORM FOR ENHANCED SOLUBILIZATION OF A POORLY SOLUBLE ACTIVE AGENT AND METHOD OF PREPARATION

TECHNICAL FIELD

The present invention relates to the field of oral dosage forms for the enhanced solubilisation of pharmaceutical, poorly soluble active ingredients. More specifically, the present invention relates to the field of oral dosage forms comprising one or more insoluble or poorly soluble active ingredients, the dosage form providing an improved dissolution profile.

INTRODUCTION

Oral administration of pharmaceutically active compounds or food supplements is one of the most convenient methods for treating a condition in a human or animal body. However, efficient absorption of the active ingredient via the gastro-intestinal tract of the treated body is a prerequisite of such administration methods.

To this purpose, the prior art has provided oral dosage forms with controlled release profiles. I.e., WO 01/15665 is directed to a pharmaceutical composition, preferably in the form of a tablet comprising a therapeutically effective amount of a medicament in a carrier comprising a water insoluble polymer and a water-insoluble inorganic salt.

WO 2005/097078 provides an oral solid compress composition comprising a magnesium salt. The composition provides a rapid dissolution of the magnesium salt, wherein not less than 75% of the magnesium salt dissolves within 45 minutes after placement in hydrochloric acid (0.1 N, 900 mL) as per USP Method <711>. In a particular embodiment, the magnesium salt is an inorganic salt such as MgO, $Mg(OH)_2$, $MgCl_2$, and others. The composition can be prepared by dry granulation, direct compression or another suitable process. The composition provides a substantially stable dissolution profile for the magnesium salt so that the dissolution profile changes only minimally even after an extended period of storage under pharmaceutically acceptable conditions when packaged in a sealed container-enclosure system. The solid composition may also exclude a cellulose-based composition. The compressed composition can be prepared and stored under anhydrous conditions.

WO 2009/150323 relates to use of a matrix for the oral administration, in tablet form, of gradual continuous release Mg provided with a protective coating slowing down the gastric dissolution of the Mg, said matrix being characterized in that it includes, for the administration (A) of 90 to 110 parts by weight of magnesium, the following ingredients: (B1) 180 to 190 parts by weight of hydroxypropylmethyl cellulose; (B2) 19.8 to 22.2 parts by weight of glyceryl behenate; (C1) 10 to 12 parts by weight of lactose; and (C2) 10 to 12 parts by weight of colloidal silica. The invention also relates to the gradual release composition including said matrix and the coating thereof.

The prior art has aimed to enhance bioresorption of such poorly water soluble or water insoluble compounds by providing sustained release dosage forms. One problem, however, is that the administered dosage of the pharmaceutically active compound may coagulate in the stomach of the patient, thereby limiting the bioaccessibility of the active ingredient for bioresorption. It is an aim of the present invention to provide oral dosage forms exhibiting fast and quantitative dissolution profiles.

SUMMARY OF THE INVENTION

In a first aspect, the present invention provides an oral dosage form comprising a granular phase and a non-granular phase, wherein said granular phase is comprised of a pharmaceutically active agent, a gas forming agent and a hydrophilic polymer.

The granular phase is provided in order to allow the oral dosage form to surface and float on the gastric fluid upon intake of the oral dosage form. Because of this floating and a prolonged stay of the pharmaceutically active ingredient in the stomach in a non-coagulated form, the dissolution can occur quickly and quantitatively.

In a second aspect, the present invention provides a method for preparing an oral dosage form, comprising the steps of:

mixing a pharmaceutically active agent, a gas forming agent and a hydrophilic polymer in presence of water, thereby obtaining a hydrated mixture;

drying said hydrated mixture, thereby obtaining granules;

mixing said granules in a non-granular powder; and compacting said granules in said non-granular powder, thereby obtaining an oral dosage form comprising a granular phase and a non-granular phase.

The preparation of the granules of the granular phase in presence of water provides a pre-treated hydrophilic polymer. Such pretreatment allows for an improved wettability of the hydrophilic polymer and consequently for an improved water influx of the granular phase during contact with the gastric fluid.

The present invention also provides an oral dosing form according to the first aspect of the invention or obtained by a method according to the second aspect of the invention, comprising a mineral for the treatment, prevention or aftertreatment of mineral deficiencies in a human or animal body, preferably in mammals.

DESCRIPTION OF THE FIGURES

By means of further guidance, figures are included to better appreciate the teaching of the present invention. Said figures are intended to assist the description of the invention and are nowhere intended as a limitation of the presently disclosed invention.

The figures and symbols contained therein have the meaning as commonly understood by one of ordinary skill in the art to which this invention belongs.

DETAILED DESCRIPTION OF THE INVENTION

Figure 1:
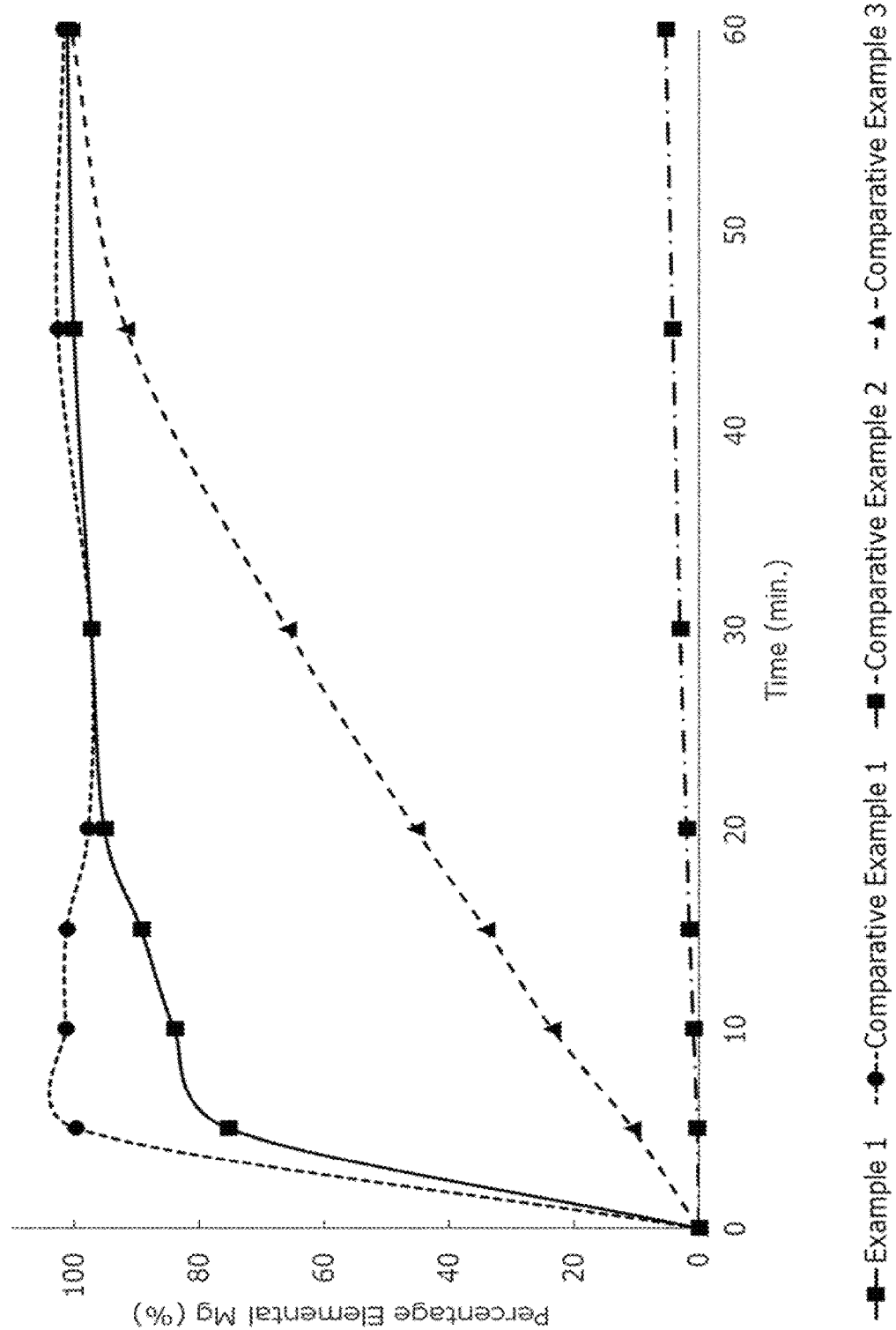
FIG. 1 shows the amount of elemental magnesium dissolved in a 0.1 N HCl solution, expressed as a percentage of the amount of elemental magnesium in the respective oral dosage forms, as a function of time (min.).

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints. All percentages are to be understood as percentage by weight and are abbreviated as "wt. %", unless otherwise defined or unless a different meaning is obvious to the person skilled in the art from its use and in the context wherein it is used.

The current invention provides in a solution for at least one of the above mentioned problems by providing an effervescent oral dosage form for controlled release and method of preparation.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The terms "elemental additive," "elemental mineral," "quantity element" or "trace element" refer to the elements of the periodic table of chemical elements: boron, sodium, magnesium, aluminium, silicium, potassium, calcium, vanadium, chromium, manganese, iron, cobalt, nickel, copper, zinc, selenium, molybdenum and barium; and more particularly: boron, magnesium, silicium, vanadium, chromium, manganese, iron, cobalt, nickel, copper, zinc, selenium and molybdenum.

A formulation according to the invention may comprise a poorly soluble, inorganic salt of an elemental additive, such as magnesium, present in an effective amount. A formulation according to the invention may comprise a poorly soluble, organic salt of an elemental additive, such as magnesium, present in an effective amount. A formulation according to the invention may comprise a poorly soluble, inorganic salt and a poorly soluble, organic salt of an elemental additive, such as magnesium, present in an effective amount. By the term "effective amount" is meant the amount or quantity of the elemental additive salt that is sufficient to elicit the required or desired response, or in other words, the amount that is sufficient to elicit an appreciable biological response when administered to a subject. When formulated into a dosage form, the composition can be present in a tablet, capsule, pill, troche, stick, granule, pellet, or powder.

As used herein, the term "patient" or "subject" are taken to mean warm blooded animals such as mammals, for example, cats, dogs, mice, guinea pigs, horses, bovine cows, sheep and humans.

In the context of the present invention, hydrophilic polymers are used to improve the performance of the solid oral composition. Exemplary hydrophilic polymers suitable for use in a insoluble pharmaceutically active ingredients, such as magnesium oxide, are described in, for example, Remington's Pharmaceutical Sciences, 18th Edition, Alfonso R. Gennaro (editor), Mack Publishing Company, Easton, PA, 1990, pp. 291-294; Alfred Martin, James Swarbrick and Arthur Commarata, Physical Pharmacy. Physical Chemical Principles in Pharmaceutical Sciences, $3^{rd}$ edition (Lea & Febinger, Philadelphia, PA, 1983, pp. 592-638); A. T. Florence and D. Altwood, Physicochemical Principles of Pharmacy, $2^{nd}$ Edition, MacMillan Press, London, 1988, pp. 281-334; R. C. Rowe, P. J. Sheskey, and P. J. Weller (eds.), Handbook of Pharmaceutical Excipients, $4^{th}$ edition, Pharmaceutical Press, London, 2003. The entire disclosures of the references cited herein are hereby incorporated by reference. Still other suitable polymers include water-soluble natural polymers, water-soluble semi-synthetic polymers (such as the water-soluble derivatives of cellulose) and water-soluble synthetic polymers. The natural polymers include polysaccharides such as inulin, pectin, algin derivatives (e.g. sodium alginate) and agar, and polypeptides such as casein and gelatin. The semi-synthetic polymers include cellulose derivatives such as methylcellulose, hydroxyethylcellulose, hydroxypropyl cellulose, their mixed ethers such as hydroxypropyl methylcellulose and other mixed ethers such as hydroxyethyl ethylcellulose and hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer). Other natural, semi-synthetic and synthetic polymers not named here which meet the criteria of water solubility, pharmaceutical acceptability and pharmacological inactivity are likewise considered to be within the ambit of the present invention.

The term "granular phase" is to be understood as a phase within an oral dosage form consisting of granules or a plurality of solid state particles having an average particle size and a particle size distribution. In the context of the present invention, such granules are prepared by fluidized bed granulation methods in an aqueous environment.

In a first aspect, the present invention provides an oral dosage form such as a tablet comprising a granular phase and a non-granular phase, wherein said granular phase is comprised of a therapeutically effective amount of pharmaceutically active agent, a gas forming agent and a hydrophilic polymer.

Upon entry in the acidic environment of the stomach, the non-granular phase of the oral dosage form dissolves quickly and water diffuses into the granules of the granular phase. The hydrophilic polymer in the granular phase absorbs the water and forms a hydrogel. Concomitantly, the gastric fluid activates the gas forming agent to form a gas, i.e. carbon dioxide formed from sodium bicarbonate. Since the gas is formed within the granular phase, gas bubbles become entrapped within the hydrogel and lower the density of the tablet. As a result, the tablet surfaces on the gastric content where the pharmaceutically active agent can dissolve into the gastric fluid without coagulation of the pharmaceutically active agent and/or early release of such coagulated phase into the intestines. Because of a prolonged residence of the pharmaceutically active ingredient in the stomach in a non-coagulated from, dissolution can occur quickly and to the fullest extent.

In a preferred embodiment, the invention provides a dosage form according to the first aspect of the invention, comprised of at least 25 wt. % of granular phase, relative to the total weight of the oral dosage form. More preferably, said oral dosage form is comprised of at least 35 wt. % of granular phase and at most 90 wt. % of granular phase, and even more preferably of 40 wt. % to 99 wt. % of granular phase. Most preferably, said oral dosage form is comprised of between 45 and 75 wt. % of granular phase and especially preferably of 46, 48, 50, 52, 54, 56, 58 or 60 wt. % of granular phase. A sufficiently large granular phase allows for providing a high content of the pharmaceutically active ingredient.

In a preferred embodiment, the invention provides a dosage form according to the first aspect of the invention, comprised of at least 1 wt. % of non-granular phase, relative to the total weight of the oral dosage form. More preferably, said oral dosage form is comprised of at least 10 wt. % or more preferably at least 25 wt. % of non-granular phase, and even more preferably of 35 wt. % to 60 wt. % of non-granular phase. Most preferably, said oral dosage form is comprised of between 40 and 55 wt. % of non-granular phase and especially preferably of 40, 42, 44, 46, 48, 50, 52, 54 wt. % of non-granular phase. A sufficiently large non-granular phase contributes to a fast disintegration of the tablet within the gastric fluid.

In a preferred embodiment, the invention provides a dosage form according to the first aspect of the invention, wherein said granular phase is prepared by aqueous based fluidized bed granulation process.

This is advantageous since pretreatment of the hydrophilic polymer with water improves its wettability, thereby affording a better influx of water in the granular phase during dissolution in the gastric fluid. Since water influx in the granular phase is an important step in the release of the pharmaceutically active ingredient, an efficient water influx is an important contributing factor in the quick release process.

In a preferred embodiment, the invention provides a dosage form according to the first aspect of the invention, wherein said hydrophilic polymer is comprised in said granular phase in an amount of at least 5.0 wt. %, and preferably in an amount of 10.0 wt. % to 25.0 wt. %, relative to the total weight of said granular phase. More preferably, said hydrophilic polymer is comprised in an amount of 10, 12, 14, 16, 18, 20 or 22 wt. %, or any amount there in between. A sufficiently high amount of hydrophilic polymer is required in order to provide a sufficiently large hydrogel upon water influx, in which hydrogel the formed gas bubbles can be entrapped.

In a preferred embodiment, the invention provides a dosage form according to the first aspect of the invention, wherein said hydrophilic polymer is selected from the group comprising methylcellulose, hydroxyethylcellulose, hydroxypropylcellulose and hydroxypropyl methylcellulose.

In a preferred embodiment, the invention provides a dosage form according to the first aspect of the invention, wherein said gas forming agent is comprised in said granular phase in an amount of 10.0 wt. % to 25.0 wt. %, relative to the total weight of said granular phase. More preferably, said gas forming agent is comprised in an amount of 10, 12, 14, 16, 18, 20 or 22 wt. %, or any amount there in between. A sufficiently high amount of gas forming agent is required in order to provide a sufficiently large amount of gas bubbles which can be entrapped within the hydrogel which is formed from said hydrophilic polymer upon water influx.

In a preferred embodiment, the invention provides a dosage form according to the first aspect of the invention, wherein said gas forming agent is a $CO_2$ releasing agent. More preferably, said gas forming agent is comprised in an amount of 10, 12, 14, 16, 18, 20 or 22 wt. %, or any amount there in between. The term "$CO_2$ releasing agent" is to be understood as a substance which upon contact with an acidic aqueous solution, releases $CO_2$ gas, such as carbonate or bicarbonate salts of sodium, potassium, calcium, etc. Preferably, said $CO_2$ releasing agent is comprised in the granular phase in an amount of from 5 to 10% by weight, more preferably in an amount of from 7.0 to 8.5% by weight. Still preferably, said $CO_2$ releasing agent is comprised in said granular phase in a ratio of about 1:3 relative to the total amount of hydrophilic polymers in said granular phase. Thus, the released $CO_2$ of the composition can be optimally embedded in the polymeric matrix for an optimal floating effect.

In a preferred embodiment, said gas forming agent is a carbon dioxide forming agent such as sodium bicarbonate, and said oral dosage form further comprises a gas activating agent which acts as a catalyst or reagent of releasing carbon dioxide. More preferably, said gas activating agent is an acidifying agent and is provided within the non-granular phase of the tablet. As used herein, the term "acidifying agent" is intended to mean a compound used to provide an acidic medium for product stability. Such compounds include, by way of example and without limitation, acetic acid, acidic amino acids, citric acid, fumaric acid and other α-hydroxy acids, hydrochloric acid, ascorbic acid, phosphoric acid, sulfuric acid, tartaric acid and nitric acid and other edible acids known to those of ordinary skill in the art. Preferably said acidifying agent is included in the non-granular phase of the composition according to the first aspect of the invention in an amount of 5 to 10% by weight, more preferably in an amount of 7.0 to 8.5% by weight.

In a preferred embodiment, the invention provides a dosage form according to the first aspect of the invention, wherein said non-granular phase comprises one or more disintegrants in an amount of at least 5 wt. % relative to the total weight of the non-granular phase. Such disintegrants promote the disruption of the solid mass into smaller particles which are more readily dispersed or dissolved. Exemplary disintegrants include, by way of example and without limitation, starches such as corn starch, potato starch, pregelatinized and modified starches thereof, sweeteners, clays, bentonite, microcrystalline cellulose (e.g., Avicel), carboxymethylcellulose calcium, croscarmellose sodium, alginic acid, sodium alginate, cellulose polyacrilin potassium (e.g., Amberlite), alginates, sodium starch glycolate, gums, agar, guar, locust bean, karaya, pectin, tragacanth, crospovidone and other materials known to one of ordinary skill in the art. In a preferred embodiment, the invention provides a dosage form according to the first aspect of the invention, wherein said granular phase comprises one or more disintegrating agents. Said disintegrating agents effect the decomposition process of a solid oral administration form such as, e.g. a tablet. Preferably, said disintegrating agent is included in the granular phase of the composition according to the first aspect of the invention in an amount of 10 to 20% by weight, more preferably in an amount of 14 to 17% by weight.

Most preferably, the invention provides an ultra-active magnesium dosage form comprising: one or more inorganic magnesium salts, one or more organic magnesium salts, one or more hydrophilic polymers and one or more disintegrating agents, said composition containing at least 2% by weight organic magnesium salts, relative to the total weight of the magnesium composition, and preferably at least 5% by weight of organic magnesium salts.

The efficiency of the absorption (relative absorption) of a magnesium salt depends among other things on the solubility in intestinal fluids. Salts with a high solubility, eg. magnesium citrate, can be absorbed better than salts with low solubility, e.g. magnesium oxide. A high dosage of organic magnesium salts offers a higher initial availability of magnesium after dissolution in an aqueous medium, such as eg. the gastric fluid. The counter-ion of the magnesium salt can also influence the absorption.

More preferably, said dosage form comprises between 10% by weight and 50% by weight of inorganic magnesium salts, relative to the total weight of the magnesium composition, and even more preferably between 20% by weight and 40% by weight. Most preferably, said composition comprises 20, 25, 30, 35 or 40% by weight of inorganic magnesium salts, or any amount included therebetween. In a preferred embodiment, the invention provides a dosage form according to the first aspect of the invention, comprising at least 10% by weight of organic magnesium salts, relative to the total weight of the magnesium salts. More preferably, said dosage form comprises between 10% by weight and 40% by weight of organic magnesium salts, relative to the total weight of the magnesium salts, and even more preferably between 20% by weight and 30% by weight. Most preferably, said composition comprises 20, 22, 24, 26, 28 or 30% by weight of organic magnesium salts, relative to the total weight of the dosage form, or any amount included therebetween.

In a preferred embodiment, the invention provides a dosage form according to the first aspect of the invention, wherein said pharmaceutically active agent has a low solubility and/or a low dissolution rate in water. By the term "low solubility", it is meant that the solubility of the pharmaceutically active agent in neutral water is less than 0.1 g/100 mL water, and more specifically less than 0.01 g/100 mL water, and even more specifically less than 0.001 g/100 mL water.

Preferably, said pharmaceutically active agent comprises an inorganic salt of an elemental additive. More preferably, said pharmaceutically active agent comprises an inorganic salt of boron, magnesium, silicium, vanadium, chromium, manganese, iron, cobalt, nickel, copper, zinc, selenium and/or molybdenum. Such oral dosage forms allow to provide supplementary amounts of quantity elements and/or essential trace elements for the mammal body or to prevent and treat diseases and conditions.

In a preferred embodiment, the invention provides a dosage form according to the first aspect of the invention, wherein said granular phase comprises one or more inorganic salts comprising one or more elemental additive, preferably selected from the group comprising boron, magnesium, silicium, vanadium, chromium, manganese, iron, cobalt, nickel, copper, zinc, selenium and/or molybdenum. In a more preferred embodiment, the invention provides a dosage form according to the first aspect of the invention, wherein the anion of said inorganic salt is selected from the group comprising oxides, carbonates, hydroxides, fluorides, chlorides, iodines, (dibasic) phosphates or sulphates of an elemental additive. More preferably, said inorganic salt is selected from the group consisting of magnesium oxide, magnesium carbonate, magnesium hydroxide, magnesium fluoride and magnesium chloride. These salts provide a high fractional content of the elemental additive. Most preferably, said inorganic salt is magnesium oxide. The present invention also includes all of the non-hydrated, hydrated, and polymorphic forms of the above-identified salts. Suppliers often use different processes for making such salts and most notably of magnesium salts. I.e., MgO from one supplier will likely have a different particle size, bulk density and/or porosity than MgO from another suppler. The present invention includes magnesium salts available in any pharmaceutically acceptable particle size range. The magnesium salts of the invention will have a bulk density and/or porosity that is suitable for use in the formulation and process of the invention. The different magnesium and other element salts are known to have different water solubility. Preferably, said one or more inorganic salts are comprised in said granular phase in an amount of 10 to 60 wt. %, more preferably in an amount of 20 to 45 wt. % and even more preferably in an amount of 25 to 40 wt. %. Most preferably, said one or more inorganic salts are comprised in said granular phase in an amount of 26, 28, 30, 32, 34, 36, 38 or 40 wt. %, or any amount there in between.

In a preferred embodiment the invention provides a dosage form according to the first aspect of the invention, comprising at least 40% by weight of magnesium salts and preferably between 40% by weight and 60% by weight of magnesium salts, relative to the total weight of said dosage form. More preferably, said composition comprises 42, 44, 46, 48, 50, 52 or 54% by weight of magnesium salts, or any value included therebetween.

In a preferred embodiment, the invention provides a dosage form according to the first aspect of the invention comprising at least 20% by weight magnesium glycerophosphate and preferably between 25% by weight and 40% by weight magnesium glycerophosphate, relative to the total weight of the dosage form. More preferably, said composition comprises 26, 28, 30, 32, 34, 36, 38 or 40% by weight magnesium glycerophosphate, or any value included therebetween.

In a preferred embodiment, the invention provides a dosage form according to the first aspect of the invention, wherein said non-granular phase comprises one or more inorganic salts comprising an elemental additive, preferably selected from the group comprising boron, magnesium, silicium, vanadium, chromium, manganese, iron, cobalt, nickel, copper, zinc, selenium and/or molybdenum. In a preferred embodiment, the invention provides a dosage form according to the first aspect of the invention, wherein said non-granular phase comprises one or more organic salts comprising an elemental additive, preferably selected from the group comprising boron, magnesium, silicium, vanadium, chromium, manganese, iron, cobalt, nickel, copper, zinc, selenium and/or molybdenum, wherein the anion is selected from the group comprising gluconates, aspartates, citrates, glycinates, glycophosphates, amino acid chelates, ascorbates, α-keto-glutarates, taurinates, tartrates, fumarates, maleates, lactates, stearates and oxalate dehydrates. More preferably, said organic salt is selected from the group consisting of magnesium gluconate, magnesium aspartate, magnesium citrate, magnesium glycinate, magnesium glycophosphate, magnesium amino acid chelate, magnesium ascorbate, magnesium c-keto-glutarate, magnesium taurinate, magnesium tartrate, magnesium fumarate, magnesium maleate, magnesium lactate, magnesium stearate and magnesium oxalate dehydrate.

In a preferred embodiment, the invention provides a dosage form according to the first aspect of the invention, wherein at least 90% of magnesium dissolves within 30 min as determined by USP method <711>. This method provides a method for determining the dissolution rate in the gastrointestinal tract. To this end, a dosage was subjected to an 0.1 N HCl solution and the concentration of dissolved elemental magnesium was monitored in time. Preferably, at least 70% of magnesium dissolves within 10 min as determined by USP method <711>, and more preferably, at least 60% of magnesium dissolves within 5 min as determined by USP method <711>. This ensures that magnesium is provided in a highly bio-available form.

In a preferred embodiment, the invention provides a dosage form according to the first aspect of the invention, wherein said dosage form is a tablet which has a thickness, a length and a width and wherein the ratio of length to width is larger than 1.1. The inventors found that a larger ratio of length to width provides a faster rise of the tablet to the surface of the aqueous dissolution liquid. A faster rise of the tablet allows for better contact and disintegration of the tablet, and consequently a faster release of the pharmaceutically active ingredient. More preferably, said ratio of length to width is larger than 1.5 and even more preferably between 1.5 and 4.0. Most preferably, said ratio is equal to 1.8, 2.0, 2.3, 2.5, 2.8, 3.0, 3.3, 3.5 or 3.8, or any value there in between.

The formulation of the present invention may further include an adsorbent, acidifying agent, antiadherent, binder, antioxidant, buffering agent, diluent (filler), alkalizing agent, bulking agent, colorant, plasticizer, stabilizer, flavor, sweetener, disintegrant, glidant, lubricant, opaquant, polishing agent, aroma, surfactant and/or other excipients known by those of ordinary skill in the art for use in formulations, or a combination thereof.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antiadherent" is intended to mean an agent that prevents the sticking of solid dosage formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "binder" is intended to mean a substance used to cause adhesion of powder particles in solid dosage formulations. Such compounds include, by way of example and without limitation, acacia, alginic acid, carboxymethylcellulose sodium, compressible sugar (e.g., NuTab), ethylcellulose, gelatin, liquid glucose, methylcellulose, povidone and pregelatinized starch. Other exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (Lutrol™ F68, Lutrol™ F127), collagen, albumin, gelatin, cellulosics in nonaqueous solvents, combinations thereof and others known to those of ordinary skill in the art. Other binders include, for example, polypropylene glycol, polyoxyethylene-polypropylene copolymer, polyethylene esters, polyethylene oxide, combinations thereof and other materials known to one of ordinary skill in the art.

As used herein, the term "diluent" or "filler" is intended to mean an otherwise inert substance used as a filler to create the desired bulk, flow properties, and compression characteristics in the preparation of solid dosage forms. Such compounds include, by way of example and without limitation, dibasic calcium phosphate, kaolin, lactose, dextrose, magnesium carbonate, sucrose, mannitol, microcrystalline cellulose, powdered cellulose, precipitated calcium carbonate, sorbitol, and starch and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, acetone, potassium metabisulfite, potassium sulfite, ascorbic acid, ascorbyl palmitate, citric acid, butylated hydroxyanisole, butylated hydroxytoluene, hypophosphorous acid, monothioglycerol, propyl gallate, sodium ascorbate, sodium citrate, sodium sulfide, sodium sulfite, sodium bisulfite, sodium formaldehyde sulfoxylate, thioglycolic acid, EDTA, pentetate, and sodium metabisulfite and others known to those of ordinary skill in the art.

As used herein, the term "buffering agent" is intended to mean a compound used to resist change in pH upon dilution or addition of acid or alkali. Such compounds include, by way of example and without limitation, acetic acid, sodium acetate, adipic acid, benzoic acid, sodium benzoate, boric acid, sodium borate, citric acid, glycine, maleic acid, monobasic sodium phosphate, dibasic sodium phosphate, HEPES, lactic acid, tartaric acid, potassium metaphosphate, potassium phosphate, monobasic sodium acetate, sodium bicarbonate, tris-sodium tartrate and sodium citrate anhydrous and dihydrate and others known to those of ordinary skill in the art.

As used herein, an aroma is a relatively volatile substance or combination of substances, or one or more water soluble palatabilty agents that produces a detectable aroma, taste, odor or scent or that mask an unwanted taste. Exemplary aromas include those generally accepted as FD&C.

As used herein, the term "glidant" is intended to mean an agent used in solid dosage formulations to promote flowability of the solid mass. Such compounds include, by way of example and without limitation, colloidal silica, cornstarch, talc, calcium silicate, magnesium silicate, colloidal silicon, tribasic calcium phosphate, silicon hydrogel and other materials known to one of ordinary skill in the art.

As used herein, the term "lubricant" is intended to mean a substance used in solid dosage formulations to reduce friction during compression. Such compounds include, by way of example and without limitation, calcium stearate, magnesium stearate, PEG, talc, mineral oil, stearic acid, and zinc stearate and other materials known to one of ordinary skill in the art.

As used herein, the term "opaquant" is intended to mean a compound used to render a coating or composition opaque. Opaquants may be used alone or in combination with a colorant. Such compounds include, by way of example and without limitation, titanium dioxide, talc and other materials known to one of ordinary skill in the art.

As used herein, the term "polishing agent" is intended to mean a compound used to impart an attractive sheen to solid dosage forms. Such compounds include, by way of example and without limitation, carnauba wax, white wax and other materials known to one of ordinary skill in the art.

As used herein, the term "stabilizer" is intended to mean a compound used to stabilize the therapeutic agent against physical, chemical, or biochemical process which would reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and other known to those of ordinary skill in the art.

The formulation of the invention can also include oils, for example, fixed oils, such as peanut oil, sesame oil, cottonseed oil, corn oil and olive oil; fatty acids, such as oleic acid, stearic acid and isostearic acid; and fatty acid esters, such as ethyl oleate, isopropyl myristate, fatty acid glycerides and acetylated fatty acid glycerides. It can also include alcohols, such as ethanol, isopropanol, hexadecyl alcohol, glycerol and propylene glycol; glycerol ketals, such as 2,2-dimethyl-1,3-dioxolane-4-methanol; ethers, such as polyethylene glycol) 450; petroleum hydrocarbons, such as mineral oil and petrolatum; or mixtures thereof.

The present invention further provides an oral dosage form comprising a granular phase and a non-granular phase, wherein said granular phase is comprised of an effervescent material comprising a pharmaceutically active agent. This is advantageous in that the effervescent material provides a matrix which resides on the gastric fluid while allowing the pharmaceutically active agent to be disintegrated by the gastric fluid. As such, it is avoided that the pharmaceutically active agent coagulates at the bottom of the stomach and is transmitted through the intestinal tract in a non-bioresorbable form. Preferably, the oral dosage form is provides such that the dosage form is able to float on top of the gastric fluid for at least 2 minutes, preferably at least 4 minutes and more preferably at least 6 minutes, at least 8 minutes or at least 10 minutes. This allows sufficient time for disintegration of the water-insoluble, pharmaceutically active agent.

In a second aspect, the present invention provides a method for preparing an oral dosage form, comprising the steps of:
  mixing a pharmaceutically active agent, a gas forming agent and a hydrophilic polymer in presence of water, thereby obtaining a hydrated mixture;
  drying said hydrated mixture, thereby obtaining granules;
  mixing said granules in a non-granular powder; and
  compacting said granules in said non-granular powder, thereby obtaining an oral dosage form comprising a granular phase and a non-granular phase.

The preparation of the granules of the granular phase in presence of water provides a pretreated hydrophilic polymer within the granular phase. Such pretreatment allows for an improved wettability of the hydrophilic polymer and consequently for an improved water influx of the granular phase during contact with the gastric fluid.

In a preferred embodiment, the invention provides a method according to the second aspect of the invention, wherein said granules are prepared by fluidized bed granulation.

In a preferred embodiment, the invention provides a method according to the second aspect of the invention, wherein said oral dosage form is provided with a thickness, a length and a width and wherein the ratio of length to width is larger than 1.1. More preferably, said ratio of length to width is larger than 1.2 and even more preferably larger than 1.5. Most preferably, said ratio is equal to 1.6, 1.7, 1.8, 1.9, 2.0, 2.2, 2.4, 2.6 or 2.8. The inventors surprisingly found that tablets having a ratio of length to width larger than 1.1 rise faster to the level of the gastric fluid.

Preferably, the invention provides a method for producing an ultraactive magnesium composition according to the first aspect of the invention, comprising the steps of:
  granulating one or more inorganic magnesium salts in a fluidized bed, thereby obtaining inorganic magnesium particles;
  surrounding said inorganic magnesium particles by one or more disintegrating agents, thereby obtaining a granular phase comprising one or more inorganic magnesium salts;
  mixing said granular phase with at least 2% by weight and preferably at least 5% by weight of one or more organic magnesium salts, relative to the total weight of the magnesium composition, thereby obtaining an ultra-active magnesium composition.

In a third aspect, the present invention provides an oral dosing form obtained by a method according to the second aspect of the invention.

In a fourth aspect, the present invention provides an oral dosing form according to the first aspect of the invention, comprising a mineral for the treatment, prevention or aftertreatment of mineral deficiencies in a human or animal body, preferably in mammals.

In a fifth aspect, the present invention provides an oral dosing according to the third aspect of the invention, comprising a mineral for the treatment, prevention or aftertreatment of mineral deficiencies in a human or animal body.

EXAMPLES

The following example is intended to further clarify the present invention, and is nowhere intended to limit the scope of the present invention.

Example 1

Magnesium oxide is mixed with a $CO_2$ releasing salt sodium bicarbonate, a hydrophilic polymer hydroxypropyl methyl cellulose, a binder polyvinylpyrrolidone and microcrystalline cellulose, and water soluble polymers in a ratio as shown in Table 1.

TABLE 1

| Composition of granular phase | |
|---|---|
| Ingredients | weight %* |
| magnesium oxide | 20 |
| hydroxypropyl methylcellulose (HPMC) | 8 |
| sodium bicarbonate | 8 |
| microcrystaline cellulose | 12 |
| polyvinylpyrrolidone | 7 |

*weight content expressed in percentage with respect to the total weight of the tablet.

The magnesium oxide is granulated in a HPMC hydrogel in a fluidized bed reactor. The formation of magnesium oxide granules is obtained by mixing magnesium oxide, hydroxypropyl methyl cellulose (HPMC), sodium bicarbonate, microcrystalline cellulose and an aqueous 22.9% by weight of polyvinyl pyrrolidone solution in a fluidized bed reactor. Air with a temperature of 60° C. is fed at a flow rate of 500 m³/h to the reactor and evacuated at a temperature of 29° C. for a period of about 3 hours. Subsequently, the obtained granules are dried at an air temperature of 70° C.

to a moisture content of less than 1.2% by weight. The accordingly obtained granular phase is isolated from the reactor.

The obtained granular phase is then mixed with a catalyst citric acid, a lubricant in the form of organic magnesium salts, a disintegrant, binder and additives according to the composition in Table 2.

TABLE 2

Composition of magnesium tablet

| Ingredients | weight %* |
|---|---|
| granular phase | 55 |
| citric acid | 7 |
| hydroxypropyl methylcellulose | 5 |
| magnesium glycerophosphate | 28 |
| vitamine B6 | 0.5 |
| magnesium stearate | 0.5 |
| polyvinylpyrrolidone | 4 |

*weight content expressed in percentage with respect to the total weight of the tablet.

The mixture with composition according to Table 2 is then pressed into a tablet at a slight feed pressure in order not to break the granular phase. In this way, tablets can be obtained with a friability/brittleness of less than 3%, a hardness of about 135 N and a moisture content of less than 3%.

Tests show that the obtained tablets float within a time span of 120 seconds in a medium of 0.1 N HCl and that complete disintegration in a medium of 0.1 N HCl under gentle stirring (100 rpm) at 36.5° C. occurs within a time span of 45 to 60 minutes.

Magnesium tablets were prepared according to the above-mentioned method, the tablets comprising 150 mg elemental magnesium as magnesium oxide and 40 mg elemental magnesium as magnesium glycerophosphate. Test results (according to USP method <711>) show that a high initial release of elementary magnesium is obtained, i.e. about 100 mg of magnesium is released within 10 min. in solution. Next, the tablet releases the remaining amount of magnesium at a predominantly constant rate. Within about 20 min., the total amount of elemental magnesium in the tablet is released into the solution.

This can be explained as follows. The non-granular phase allows a rapid penetration of water into the tablet as soon as the tablet ends up in the aqueous medium of the stomach. Accordingly, the non-granular phase quickly disintegrates and releases the granular stage as granules. Water then penetrates within the granular phase and hydrates HPMC, as a result of which HPMC swells and forms a hydrogel.

The water, and more in particular the acidic gastric fluid, also activates the $CO_2$ releasing agent in the granules, so that the released $CO_2$ is retained in the hydrogel. The tablet is floating by the enclosed gas volumes into the aqueous medium and releases granular particles in the aqueous medium. Floating in the aqueous medium, however, the tablet absorbs less water and when a certain amount of $CO_2$ has been activated and released, the tablet will sink again and activate a new $CO_2$ releasing agent. The composition and structure of the tablet in this manner regulates the residence time of the tablet and the release efficiency of magnesium in the stomach. In this way, an improved solubility of magnesium in the gastric fluid can be achieved, and a better absorption of magnesium in the body.

Thus, the composition and the oral dosage form according to the present invention is extremely suitable for a rapid, initial absorption and subsequently a gradual and complete absorption of elementary magnesium in a human or animal body.

The oral dosage form of Example 1 was tested with respect to dissolution rate in the gastro-intestinal tract using USP method <711>. To this end, a dosage was subjected to an 0.1 N HCl solution and the concentration of dissolved elemental magnesium was monitored in time. The results were also compared to oral dosage forms for supplementing magnesium known in the market, as described in Comparative Examples 1 to 3.

TABLE 3

Oral dosage form of Comparative Examples.

| COMPARATIVE EXAMPLE 1 | Powder comprising 3 g of magnesium gluconate (corresponding to 162 mg elemental magnesium), macrogol 6000 and colloidal silicium dioxide. |
|---|---|
| COMPARATIVE EXAMPLE 2 | Capsule comprising 450 mg of elemental magnesium. |
| COMPARATIVE EXAMPLE 3 | Tablet comprising 900 mg of magnesium glycerophosphate (corresponding to 100 mg of elemental magnesium), 1 mg vitamine B6, 12.5 µg vitamine B12, 100 µg vitamine B9, 150 mg taurine 150 mg and 12.5 µg vitamine D. |

Figure 2:
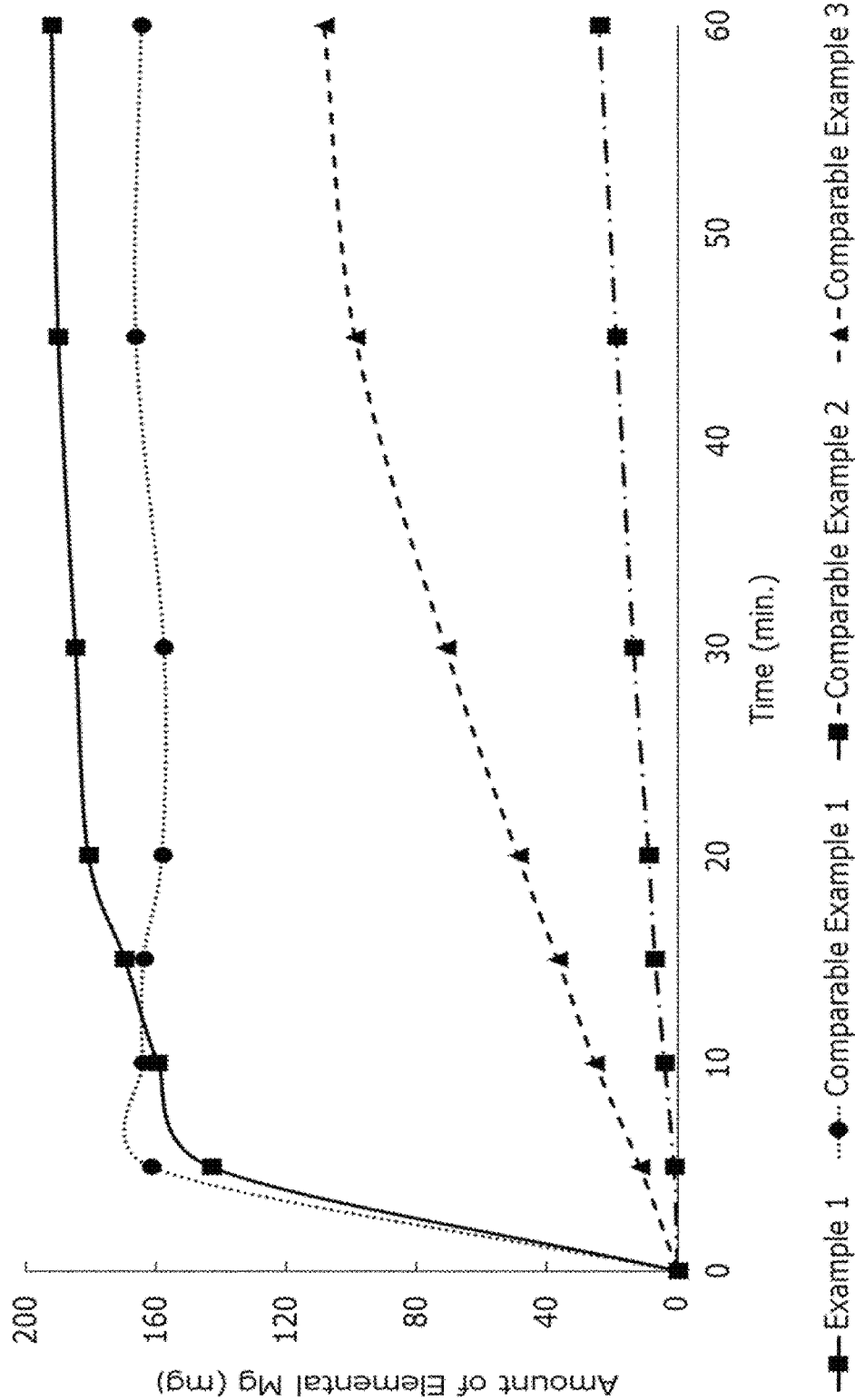
FIG. 2 shows the absolute amount of elemental magnesium dissolved in the 0.1 N HCl solution, as a function of time (min.).

The results are depicted in FIGS. 1 and 2. FIG. 1 shows the amount of elemental magnesium dissolved in the 0.1 N HCl solution, expressed as a percentage of the amount of elemental magnesium in the respective oral dosage forms, as a function of time (min.). FIG. 2 shows the absolute amount of elemental magnesium dissolved in the 0.1 N HCl solution, as a function of time (min.).

The result show that the tablet according to Example 1 shows complete dissolution of 80% of all elemental magnesium within 10 min., see FIG. 1. This corresponds to about 160 mg, see FIG. 2.

The results further show that Comparative Example 1 shows a nearly complete dissolution of the elemental magnesium. This can readily be explained by the fact that the powder of Comparative Example 1 consists of an organic magnesium salt, in a non compressed powder formulation which are known to provide faster dissolution rates. Such dosage forms have, however, a relatively low magnesium content and are unwieldy in use in that the user either needs to consume several doses per day in the case of compacted or encapsulated dosage forms or in the case of powder dosage forms, needs to consume these as a water soluble powder in bulk sachets or stick packs.

Comparing the behaviour of an inorganic magnesium tablet according to Example 1 with the behaviour of an organic magnesium powder according to Comparative Example 1 leads to the conclusion that the tablet according to the invention provides a comparable efficiency in delivering elemental magnesium in a fluid.

The tablet of Comparable Example 3 comprises an organic magnesium salt, like the powder of Comparative Example 1. The results in FIGS. 1 and 2 clearly show that the tablet dosage form shows a slower dissolution of elemental magnesium. This can be readily understood by the fact that the tablet matrix needs to be at least partially disintegrated before the organic magnesium salt can be contacted with water and dissolved therein.

In contrast, the capsule according to Comparative Example 2 provides a significantly slower release of elemental magnesium and has released less than 10% of its total amount of elemental magnesium within one hour. This means that the capsule will have left the stomach before the elemental magnesium can be brought in solution.

Concludingly, tablets can be considered a preferred oral dosage form as they are easy to use and provide accurate and high quantities of nutrients, elements or active ingredients. However, tabletting generally delays the release of the nutrient, element or active ingredient in the gastric fluid. As a consequence, the the tablet risks being emptied from the stomach into the intestinal tract before its entire dissolution, thereby limiting its bioaccessability.

Using a tablet comprising a non-granular matrix comprising therein effervescent granules of active ingredients allows the intake of a tablet that can be dissolved in the gastric fluid in a manner similar to bulk powder dosages.

The invention claimed is:

1. An oral gastro-intestinal dosage form for treatment of a mineral deficiency consisting of a granular phase and a non-granular phase,
   wherein said granular phase comprises magnesium oxide, a carbonate or bicarbonate salt, and a hydrophilic polymer,
   wherein the magnesium oxide is in an amount of 10 to 50 wt. % relative to a total weight of the dosage form, the carbonate or bicarbonate salt is comprised in an amount of 5 wt. % to 10 wt. % relative to a total weight of the dosage form and the hydrophilic polymer in an amount of 5.0 wt. % to 25.0 wt. % relative to a total weight of the granular phase,
   wherein an edible acid is included in the non-granular phase of the composition in an amount of 5.0 to 10.0 wt. % relative to the total weight of the dosage form, and
   wherein said non-granular phase of the composition further comprises one or more organic magnesium salts in an amount of 20.0 to 50.0 wt. % relative to the total weight of the dosage form, wherein said oral gastro-intestinal dosage form is able to float on top of gastric acid upon contact therewith for at least 2 minutes.

2. The oral gastro-intestinal dosage form according to claim 1, wherein said one or more organic magnesium salt is magnesium glycerophosphate.

3. The oral gastro-intestinal dosage form according to claim 1, wherein at least 90% of magnesium dissolves within 30 min. as determined by USP method <711>.

4. The oral gastro-intestinal dosage form according to claim 1, wherein at least 60% of magnesium dissolves within 5 min. as determined by USP method <711>.

5. The oral gastro-intestinal dosage form according to claim 1, wherein said hydrophilic polymer is selected from the group consisting of methylcellulose, hydroxyethylcellulose, hydroxypropylcellulose and hydroxypropyl methylcellulose.

6. The oral gastro-intestinal dosage form according to claim 1, wherein said edible acid is an α-hydroxy acid.

7. The oral gastro-intestinal dosage form according to claim 1, wherein the granular phase is in an amount of 55.0 wt. % to 99.0 wt. % relative to the total weight of the dosage form and the non-granular phase is in an amount of 1.0 wt. % to 45.0 wt. % relative to the total weight of the dosage form.

8. An oral gastro-intestinal dosage form for treatment of a mineral deficiency consisting of a granular phase and a non-granular phase,
   wherein said granular phase comprises magnesium oxide, a carbonate or bicarbonate salt, and a hydrophilic polymer,
   wherein the magnesium oxide is in an amount of 20 wt. % relative to a total weight of the dosage form, the carbonate or bicarbonate salt is comprised in an amount of 8.0 wt. % relative to the total weight of the dosage form, and the hydrophilic polymer in an amount of 8.0 wt. % relative to a total weight of the dosage form,
   wherein an edible acid is included in the non-granular phase of the composition in an amount of 7.0 wt. % relative to the total weight of the dosage form, and
   wherein said non-granular phase of the composition further comprises one or more organic magnesium salts in an amount of 20.0 to 50.0 wt. % relative to the total weight of the dosage form.

9. The oral gastro-intestinal dosage form according to claim 8, wherein the one or more magnesium salts is in an amount of 28.5 wt. % relative to the total weight of the dosage form.

10. The oral gastro-intestinal dosage form according to claim 1, wherein the granular phase is in an amount of 55.0 wt. % relative to the total weight of the dosage form and the non-granular phase is in an amount of 45.0 wt. % relative to the total weight of the dosage form.

11. The oral gastro-intestinal dosage form according to claim 1, wherein said non-granular phase further comprises one or more disintegrants in an amount of at least 5 wt. % relative to the total weight of the non-granular phase.

12. The oral gastro-intestinal dosage form according to claim 1, wherein said oral gastro-intestinal dosage form is able to float on top of gastric acid upon contact therewith for at least 2 minutes to at least 10 minutes.

* * * * *